(12) United States Patent
Mukade et al.

(10) Patent No.: US 11,739,038 B2
(45) Date of Patent: Aug. 29, 2023

(54) METHOD FOR PRODUCING AZOLE DERIVATIVE, BROMOHYDRIN DERIVATIVE AND METHOD FOR PRODUCING SAME, AND METHOD FOR PRODUCING 1-CHLORO-3-(4-CHLOROPHENOXY)BENZENE

(71) Applicant: Kureha Corporation, Tokyo (JP)

(72) Inventors: Tsutomu Mukade, Tokyo (JP); Hiroshi Hoshino, Tokyo (JP); Hisataka Kobayashi, Tokyo (JP); Rumi Sano, Tokyo (JP); Natsuki Nemoto, Tokyo (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 17/905,570

(22) PCT Filed: Mar. 10, 2021

(86) PCT No.: PCT/JP2021/009622
§ 371 (c)(1),
(2) Date: Sep. 2, 2022

(87) PCT Pub. No.: WO2021/182530
PCT Pub. Date: Sep. 16, 2021

(65) Prior Publication Data
US 2023/0122400 A1 Apr. 20, 2023

(30) Foreign Application Priority Data
Mar. 10, 2020 (JP) .................. 2020-041195

(51) Int. Cl.
*C07C 41/24* (2006.01)
*C07D 249/08* (2006.01)

(52) U.S. Cl.
CPC ............ *C07C 41/24* (2013.01); *C07D 249/08* (2013.01)

(58) Field of Classification Search
CPC .................................................. C07C 41/24
See application file for complete search history.

(56) References Cited

U.S. PATENT DOCUMENTS

| | | | |
|---|---|---|---|
| 4,584,307 A | 4/1986 | Richardson et al. | |
| 4,766,253 A | 8/1988 | Rauber | |
| 5,283,378 A | 2/1994 | Bielefeldt et al. | |
| 10,945,434 B2 | 3/2021 | Harigae et al. | |
| 2006/0167301 A1 | 7/2006 | Yamada et al. | |
| 2014/0141974 A1 | 5/2014 | Dietz et al. | |
| 2020/0288714 A1 | 9/2020 | Harigae et al. | |

FOREIGN PATENT DOCUMENTS

| | | | |
|---|---|---|---|
| CA | 2031444 A1 | 6/1991 | |
| CN | 1810774 A | 8/2006 | |
| CN | 101423460 A | 5/2009 | |
| CN | 102516044 A | 6/2012 | |
| CN | 103814017 A | 5/2014 | |
| CN | 105198713 A | 12/2015 | |
| CN | 108069834 A | 5/2018 | |
| EP | 0431487 A1 * | 6/1991 | ............ C07C 41/16 |
| JP | S60-56966 A | 4/1985 | |
| JP | S62281837 A | 12/1987 | |
| JP | S6341434 A | 2/1988 | |
| JP | H04273834 A | 9/1992 | |
| JP | 2014-520833 A | 8/2014 | |
| WO | 2019/093522 A1 | 5/2019 | |

OTHER PUBLICATIONS

Office Action for CN Application No. 202180014358.8, dated Nov. 23, 2022, 5 pages.
English translation of Office Action for CN Application No. 202180014358.8, dated Nov. 23, 2022, 8 pages.
Takayoshi Hara et al., "Highly efficient dehalogenation using hydroxyapatite-supported palladium nanocluster catalyst with molecular hydrogen", Green Chem., vol. 6, pp. 507-509, 2004.
English translation of the Written Opinion of the International Searching Authority for PCT/JP2021/009622, dated Sep. 22, 2022, 7 pages.
Office Action for JP Application No. 2022-50726, dated Sep. 6, 2022, 2 pages.
English translation of Office Action for JP Application No. 2022-50726, dated Sep. 6, 2022, 3 pages.
Office Action for JP Application No. 2022-507256, dated Sep. 6, 2022, 2 pages.
English translation of Office Action for JP Application No. 2022-507256, dated Sep. 6, 2022, 3 pages.

* cited by examiner

*Primary Examiner* — Rosalynd A Keys
(74) *Attorney, Agent, or Firm* — Abel Schillinger, LLP

(57) ABSTRACT

A novel method of producing 1-chloro-3-(4-chlorophenoxy)benzene can include performing hydrogenation reduction of 1-bromo-2-chloro-4-(4-chlorophenoxy)benzene or 1-bromo-4-chloro-2-(4-chlorophenoxy)benzene.

1 Claim, No Drawings

METHOD FOR PRODUCING AZOLE DERIVATIVE, BROMOHYDRIN DERIVATIVE AND METHOD FOR PRODUCING SAME, AND METHOD FOR PRODUCING 1-CHLORO-3-(4-CHLOROPHENOXY)BENZENE

TECHNICAL FIELD

The present invention relates to a method of producing an azole derivative, a bromohydrin derivative, a method of producing the same, and a method of producing 1-chloro-3-(4-chlorophenoxy)benzene.

BACKGROUND ART

There has been a need for agricultural and horticultural chemicals having low toxicity to humans and animals and excellent safety in handling, and exhibiting a high controlling effect against a wide variety of plant diseases. Azole fungicides are known as an agricultural or horticultural chemical exhibiting a high controlling effect (Patent Document 1).

CITATION LIST

Patent Document

Patent Document 1: WO 2019/093522 A1
Patent Document 2: JP 2014-520833 T

SUMMARY OF INVENTION

Technical Problem

Patent Document 1 discloses a plurality of synthesis methods through a phenylpyruvate derivative as a method of synthesizing compounds described in Patent Document 1. More specifically, Patent Document 1 discloses (1) a method of obtaining a phenylpyruvate derivative by oxidation and esterification of an acetophenone derivative, (2) a method of obtaining a phenylpyruvate derivative by acylation through Friedel-Crafts reaction, and (3) a method of obtaining a phenylpyruvate derivative by reaction of an organometallic reagent, which is formed by transmetalation reaction of a halobenzene compound, with a dialkyl oxalate or an alkyl chloroglyoxylate.

However, the method by oxidation and esterification of an acetophenone derivative needs to use expensive iodine or methyl iodide. In addition, in the method of acylation by Friedel-Crafts reaction, strongly acidic liquid waste containing aluminum needs to be treated. Furthermore, the method by reaction of an organometallic reagent and a dialkyl oxalate or the like needs to be performed at extremely low temperatures when an alkyllithium reagent is used. On the other hand, when a Grignard reagent is used, the method has a problem of low yield.

Thus, the present invention has been made in view of the above problems, and an object of the present invention is to provide a novel method of producing an azole derivative that can solve the problems described above.

Solution to Problem

A method of producing an azole derivative according to an embodiment of the present invention is a method of producing an azole derivative represented by General Formula (I) to solve the above problems:

[Chem. 1]

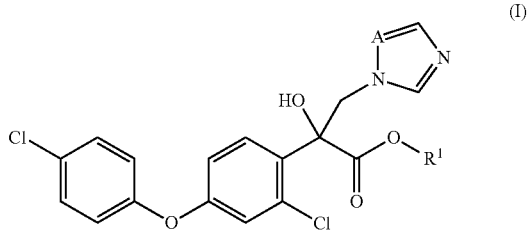

wherein in Formula (I), A is N or CH; and $R^1$ is a $C_1$-$C_6$-alkyl group, the method including:

reacting an organometallic reagent formed from 1-bromo-2-chloro-4-(4-chlorophenoxy)benzene by transmetalation reaction with a bromopyruvic acid derivative represented by $CH_2BrCOCOOR^1$ to obtain a bromohydrin derivative represented by General Formula (II):

[Chem. 2]

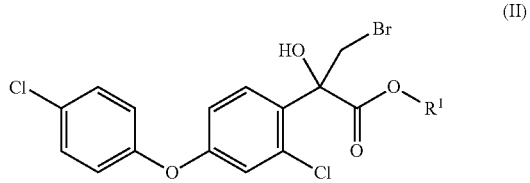

wherein in Formula (II), $R^1$ is identical to $R^1$ in Formula (I); and reacting the bromohydrin derivative with imidazole, 1,2,4-triazole, or an alkali metal salt thereof to obtain the azole derivative.

ADVANTAGEOUS EFFECTS OF INVENTION

The method of producing an azole derivative according to an embodiment of the present invention can reduce the production cost compared with the production methods in the art.

DESCRIPTION OF EMBODIMENTS

A suitable embodiment for implementing the present invention will now be explained. The embodiment described below illustrates an example of a representative embodiment of the present invention, and the scope of the present invention is not to be construed narrowly by this.

1. Method of Producing Azole Derivative

A method of producing an azole derivative according to the present embodiment is a method of producing an azole derivative represented by General Formula (I) below (hereinafter referred to as "azole derivative (I)").

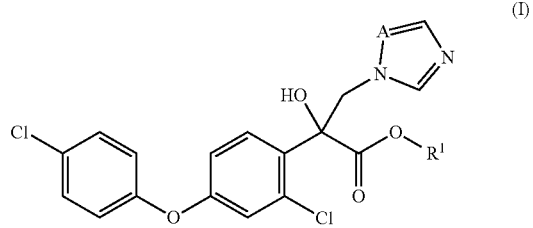

In General Formula (I), A is N or CH and is suitably N.

In General Formula (I), $R^1$ is a $C_1$-$C_6$-alkyl group. The $C_1$-$C_6$-alkyl group is a linear or branched alkyl group having 1 to 6 carbon atoms, and examples thereof include a methyl group, an ethyl group, a 1-methylethyl group, a 1,1-dimethylethyl group, a propyl group, a 1-methylpropyl group, a 2-methylpropyl group, a 1,1-dimethylpropyl group, a 2,2-dimethylpropyl group, a 1-ethyl propyl group, a butyl group, a 1-methylbutyl group, a 2-methylbutyl group, a 3-methylbutyl group, a 3,3-dimethylbutyl group, a 2,2-dimethylbutyl group, a 1,1-dimethylbutyl group, a 1-ethylbutyl group, a 2-ethylbutyl group, a pentyl group, a 1-methylpentyl group, a 2-methylpentyl group, a 3-methylpentyl group, and a 4-methylpentyl group.

Method of Producing Azole Derivative (I)

As shown in synthesis scheme 1 below, the method of producing an azole derivative (I) according to the present embodiment includes:
obtaining a bromohydrin derivative represented by General Formula (II) from 1-bromo-2-chloro-4-(4-chlorophenoxy)benzene; and
obtaining the azole derivative (I) by azolation of the resulting bromohydrin derivative.

(Synthesis scheme 1)

[Chem. 4]

(Step 1) A bromohydrin derivative represented by General Formula (II) (hereinafter referred to as bromohydrin derivative (II)) is obtained from 1-bromo-2-chloro-4-(4-chlorophenoxy)benzene represented by Formula (III) (hereinafter referred to as compound (III)). Specifically, an organometallic reagent formed from the compound (III) by transmetalation reaction is reacted with a bromopyruvic acid derivative represented by $CH_2BrCOCOOR^1$ in a solvent to obtain the bromohydrin derivative (II). Examples of the transmetalation reagent used in the transmetalation reaction include methyllithium, butyllithium, isopropylmagnesium chloride, and an isopropylmagnesium chloride-lithium chloride complex, and an isopropylmagnesium chloride-lithium chloride complex is preferably used. Examples of the solvent include tetrahydrofuran, 2-methyltetrahydrofuran, 4-methyltetrahydropyran, cyclopentyl methyl ether, diethyl ether, methyl tertiary-butyl ether, and cyclopentyl methyl ether, and tetrahydrofuran is suitably used. The reaction in step 1 can be performed at a temperature of −30 to 50° C. and can be suitably performed at −10 to 30° C. The transmetalation reaction provides a maximum amount of organometallic reagent at a reaction time of 5 minutes to 3 hours but suitably provides a maximum amount of organometallic reagent at 30 minutes to 2 hours. A solution of the organometallic reagent can be added to a solution of a bromopyruvic acid derivative in a separate container, or a bromopyruvic acid derivative can be added to a solution of the organometallic reagent. Suitably, the bromopyruvic acid derivative is added to a solution of the organometallic reagent.

(Step 2) The azole derivative (I) is obtained through azolation of the bromohydrin derivative (II) by reacting the bromohydrin derivative (II) with imidazole, 1,2,4-triazole, or an alkali metal salt thereof in a solvent. Specifically, the compound (II), imidazole or 1,2,4-triazole, and a base are reacted in an organic solvent, or the compound (II) and an alkali metal salt of imidazole or 1,2,4-triazole are reacted in an organic solvent, and the azole derivative (I) is obtained. Examples of the reagent used in the azolation reaction include a combination of imidazole or 1,2,4-triazole with sodium carbonate, or a sodium salt of imidazole or 1,2,4-triazole, and a sodium salt of 1,2,4-triazole is suitably used. Examples of the solvent include dimethylformamide, dimethylacetamide, and N-methylpyrrolidone, and dimethylformamide is suitably used. The reaction in step 2 can be performed at a temperature of 0 to 150° C. and can be suitably performed at 40 to 80° C.

As described above, the method of producing the azole derivative (I) in the present embodiment eliminates the need to use expensive iodine or methyl iodine, which has been required in methods in the art. Thus, the method can reduce the production cost compared with methods in the art. In addition, methods in the art have caused problems of producing a large amount of inorganic salt as a by-product and further generating odor from a DMSO decomposition product, but the production method according to the present embodiment can avoid the problems of the production of an inorganic salt as a by-product and the generation of odor from a DMSO decomposition product.

Method of Producing 1-bromo-2-chloro-4-(4-chlorophenoxy)benzene (Compound (III))

The compound (III) used in the production of the azole derivative (I) described above can be obtained, for example, by condensation reaction of 4-chlorophenol and 1-bromo-2,4-dichlorobenzene or 1-bromo-2-chloro-4-fluorobenzene according to a method described in Patent Document 2 described above. However, in the method according to the present embodiment, the compound (III) is synthesized from 1-chloro-3-(4-chlorophenoxy)benzene as shown in synthesis scheme 2 below.

(Synthesis scheme 2)

[Chem. 5]

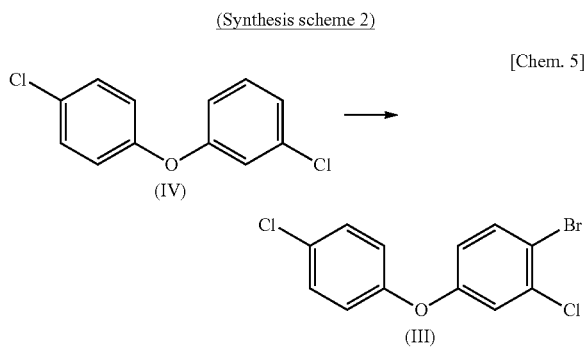

In the method according to the present embodiment, the compound (III) is obtained by reacting 1-chloro-3-(4-chlorophenoxy)benzene represented by Formula (IV) with a brominating agent. For the brominating agent, bromine or a bromine compound is used. Examples of the bromine compound includes, but are not limited to, preferably brominated imides, more preferably brominated cyclic imides, such as N-bromosuccinimide and 1,3-dibromo-5,5-dimethylhydantoin. The amount of bromine or bromine compound used is exemplified by from 1 to 3 equivalents, but an amount of 1 to 1.3 equivalents is preferably used in terms of cost. However, when a bromine compound having two reactive bromines in the molecule, such as 1,3-dibromo-5,5-dimethylhydantoin, is used, an amount of 0.5 to 1.3 equivalents is preferably used. Examples of the solvent include acetonitrile and acetic acid, but the reaction is most preferably performed without solvent in terms of cost. When the brominating agent is a bromine compound, a small amount of iodine or bromine can be added as a catalyst as necessary. The bromination reaction can be performed at a temperature of −20 to 70° C. but is preferably performed in a range of 0 to 30° C. to selectively obtain the compound (III). When bromination is performed without solvent, the reaction solution may solidify as the formation of the compound (III) with a low melting point proceeds. Thus, when the bromination is performed without solvent, starting the reaction at or near 0° C. and gradually increasing the temperature to approximately 30° C. according to the progress of the reaction are effective in improving the selectivity of the compound (III).

1-Chloro-3-(4-chlorophenoxy)benzene used in the present embodiment is a much less expensive compound (approximately from 1/400 to 1/500 in price) than 1-bromo-2,4-dichlorobenzene and 1-bromo-2-chloro-4-fluorobenzene used in a method described in Patent Document 2. Thus, the method of the present embodiment can suppress the increase in the production cost.

In the reaction according to synthesis scheme 2, the target compound (III) can be obtained with high selectivity, such as 93% or higher, 95% or higher, or 97% or higher. On the other hand, 1-bromo-4-chloro-2-(4-chlorophenoxy)benzene represented by Formula (V) below (hereinafter referred to as compound (V)), a regioisomer of the compound (III), is also formed.

[Chem. 6]

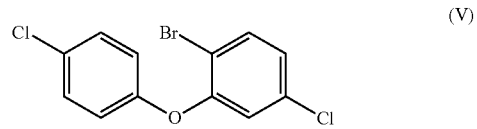

Thus, in the present embodiment, the compound (III) can be purified from a mixture containing the compound (V) by repulp washing the mixture with an alcoholic solvent before subjecting to the reaction of synthesis scheme 1. The repulp washing is performed on a solid obtained by post-treatment of the reaction mixture obtained in the reaction according to synthesis scheme 2. In particular, when the brominating agent is bromine, the solid obtained by concentrating the reaction mixture can be used as is, and thus this is advantageous. The solid is preferably pulverized using a mortar or the like before subjecting to the repulp washing. Examples of the alcoholic solvent include 2-propanol, ethanol, and methanol, and 2-propanol is suitably used. The solid after the repulp washing is dried under reduced pressure and is used as the compound (III) in step 2. The repulp washing can increase the ratio of the compound (III) to, for example, 95% or higher, 97% or higher, or 99% or higher. From the viewpoint of preventing loss by washing, the alcoholic solvent used in the repulp washing is preferably cooled, for example, to 0 to 10° C. for use. In addition, from a similar viewpoint, the amount of alcoholic solvent used is preferably as small as possible. Specifically, the amount is preferably approximately from 50% to 200% of the solid.

A repulp wash solution, the filtrate from the repulp washing, also contains the compound (III) together with the compound (V). Thus, in the present embodiment, the compound (IV) described above can be obtained by debromination by hydrogenation reduction of the compound (III) and the compound (V) contained in the repulp wash solution. The hydrogenation reduction is performed by catalytic reduction of the compound (III) and the compound (V) in a hydrogen atmosphere using a palladium-based catalyst, such as palladium on carbon. Compared with the elimination reduction of bromine, the elimination reduction of chlorine is significantly slow. Thus, performing the hydrogenation reduction of the present embodiment allows the debromination to proceed preferentially, and the compound (IV) can be efficiently obtained.

The repulp wash solution contains the compound (III) and the compound (V). Thus, discarding the wash solution causes the environmental load due to incineration and the cost increase due to the loss of raw material. Purification and recovery of the compound (IV) from the repulp wash solution can reduce the environmental load and suppress the cost increase due to the loss of raw material.

SUMMARY

As described above, the method of producing an azole derivative according to an embodiment of the present invention is a method of producing an azole derivative represented by General Formula (I) described above and includes: reacting an organometallic reagent formed from 1-bromo-2-chloro-4-(4-chlorophenoxy)benzene by transmetalation reaction with a bromopyruvic acid derivative represented by $CH_2BrCOCOOR^1$ to obtain a bromohydrin derivative represented by General Formula (II) described above; and reacting the bromohydrin derivative with imidazole, 1,2,4-triazole, or an alkali metal salt thereof to obtain the azole derivative.

In an aspect of the method of producing an azole derivative according to an embodiment of the present invention, the method further includes reacting 1-chloro-3-(4-chlorophenoxy)benzene with bromine or a bromine compound to obtain 1-bromo-2-chloro-4-(4-chlorophenoxy)benzene.

In an aspect of the method of producing an azole derivative according to an embodiment of the present invention, the bromine compound is a brominated imide.

In an aspect of the method of producing an azole derivative according to an embodiment of the present invention, the method further includes purifying the resulting 1-bromo-2-chloro-4-(4-chlorophenoxy)benzene by repulp washing with an alcoholic solvent.

In addition, the bromohydrin derivative according to an embodiment of the present invention is a bromohydrin derivative represented by General Formula (II) described above.

Furthermore, a method of producing the bromohydrin derivative according to an embodiment of the present invention is a method in which an organometallic reagent formed from 1-bromo-2-chloro-4-(4-chlorophenoxy)benzene by transmetalation reaction is reacted with a bromopyruvic acid derivative represented by $CH_2BrCOCOOR^1$ to obtain the bromohydrin derivative.

The method of producing 1-chloro-3-(4-chlorophenoxy)benzene according to an embodiment of the present invention is a method in which 1-chloro-3-(4-chlorophenoxy)benzene is obtained by performing hydrogenation reduction of 1-bromo-2-chloro-4-(4-chlorophenoxy)benzene or a mixture of 1-bromo-2-chloro-4-(4-chlorophenoxy)benzene and its regioisomer.

Embodiments of the present invention will be described in further detail hereinafter using examples. The present invention is not limited to the examples below, and it goes without saying that various aspects are possible with regard to the details thereof. Furthermore, the present invention is not limited to the embodiments described above, and various modifications are possible within the scope indicated in the claims. Embodiments obtained by appropriately combining the technical means disclosed by the embodiments are also included in the technical scope of the present invention. In addition, all of the documents described in the present specification are herein incorporated by reference.

EXAMPLES

Synthesis Example 1: Synthesis 1 of methyl 2-(2-chloro-4-(4-chlorophenoxy)phenyl)-2-hydroxy-3-(1H-1,2,4-triazol-1-yl)propanoate Synthesis of methyl 3-bromo-2-(2-chloro-4-(4-chlorophenoxy)phenyl) hydroxypropanoate

[Chem. 7]

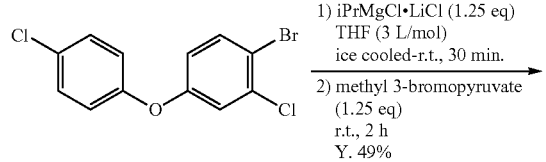

1) iPrMgCl·LiCl (1.25 eq)
   THF (3 L/mol)
   ice cooled-r.t., 30 min.
2) methyl 3-bromopyruvate
   (1.25 eq)
   r.t., 2 h
   Y. 49%

-continued

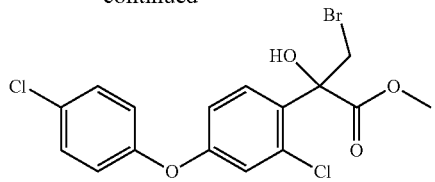

A solution of 1-bromo-2-chloro-4-(4-chlorophenoxy)benzene (purity 99.5 GC area%, 0.203 g) in tetrahydrofuran (1.9 mL) was cooled in an ice bath, an isopropylmagnesium chloride-lithium chloride complex and a tetrahydrofuran solution (1.27 mol/L, 0.628 mL, 0.798 mmol) were added, and the mixture was stirred under room temperature for 30 minutes. The solution was cooled in an ice bath, and methyl 3-bromopyruvate (0.147 g) was added and stirred under room temperature for 2 hours. A saturated aqueous ammonium chloride solution (2 mL) was added to quench the reaction, and then the mixture was extracted with ethyl acetate (1 mL×3). Water (2 mL) was added to the extract, and the mixture was extracted with ethyl acetate (1 mL×3). The extract was dried with $Na_2SO_4$, and then the solvents were distilled off. The crude purified product (0.2827 g) thus obtained was purified by silica gel column chromatography, and methyl 3-bromo-2-(2-chloro-4-(4-chlorophenoxy)phenyl)-2-hydroxypropanoate (0.130 g, 48.5% yield) was obtained.

$^1$H NMR (400 MHz, $CDDl_3$) δ 7.55 (d, J=8.8 Hz, 1H), 7.37-7.32 (m, 2H), 7.01-6.97 (m, 2H), 6.99 (d, J=2.6 Hz, 1H), 6.91 (dd, J=8.8 Hz, 2.6 Hz, 1H), 4.17 (d, J=10.6 Hz, 1H), 4.12 (d, J=10.6 Hz, 1H), 3.83 (s, 3H), 3.81 (s, 1H).

Synthesis of methyl 2-(2-chloro-4-(4-chlorophenoxy)phenyl)-2-hydroxy-3-(1H-1,2,4-triazol-1-yl)propanoate

[Chem. 8]

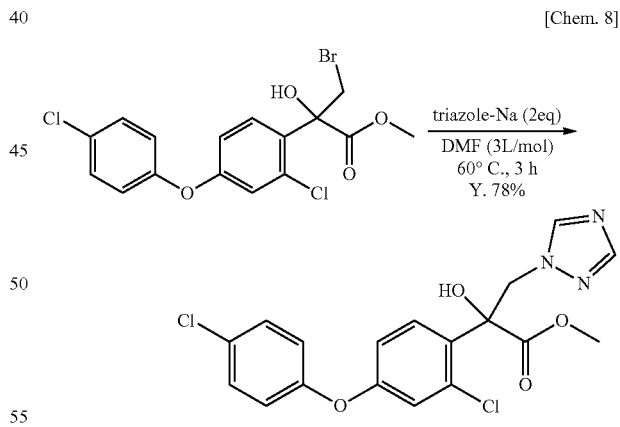

triazole-Na (2eq)
DMF (3L/mol)
60° C., 3 h
Y. 78%

Methyl 3-bromo-2-(2-chloro-4-(4-chlorophenoxy)phenyl)-2-hydroxypropanoate (0.130 g) obtained in the above synthesis was dissolved in DMF (0.9 mL), a sodium triazole salt (0.057 g) was added, and the mixture was stirred in an oil bath (60° C.) for 3 hours. After stirring, the mixture was cooled to room temperature, and the solvent was distilled off. Ethyl acetate (2 mL) was added thereto, further a saturated brine solution (2 mL) was added, and the organic layer was separated. The aqueous layer was extracted with ethyl acetate (1 mL×3) and dried with $Na_2SO_4$, and then the solvents were distilled off. The residue thus obtained was purified by silica gel column chromatography, and methyl 2-(2-chloro-4-(4-chlorophenoxy)phenyl)-2-hydroxy-3-(1H-1,2,4-triazol-1-yl)propanoate (0.099 g, 78.4% yield, a white individual) was obtained.

$^1$H NMR (400 MHz, CDDl$_3$) δ 8.00 (s, 1H), 7.89 (s, 1H), 7.41 (d, J=8.8 Hz, 1H), 7.36-7.33 (m, 2H), 6.98-6.95 (m, 3H), 6.81 (dd, J=8.8 Hz, 2.6 Hz, 1H), 5.02 (d, J=14.3 Hz, 1H), 4.93 (d, J=14.3 Hz, 1H), 4.83 (s, 1H), 3.8 (s, 3H).

Synthesis Example 2: Synthesis 2 of methyl 2-(2-chloro-4-(4-chlorophenoxy)phenyl)-2-hydroxy-3-(1H-1,2,4-triazol-1-yl)propanoate

[Chem. 9]

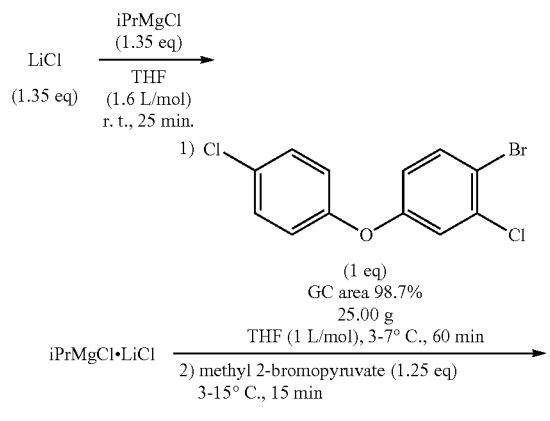

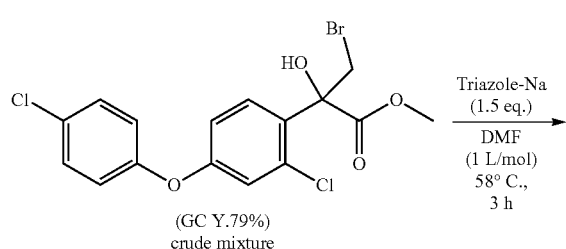

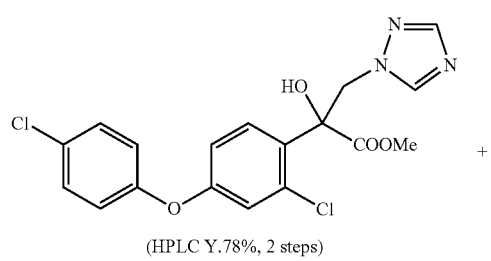

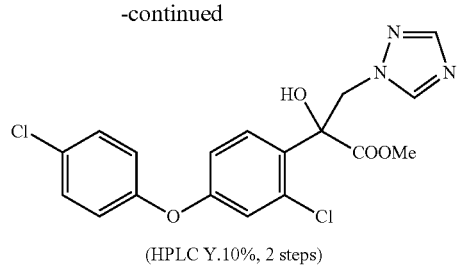

Lithium chloride (4.499 g, vacuum-dried at 130° C. for 6 hours) was weighed under a stream of nitrogen and sealed in a 500-mL four-neck flask equipped with a dropping funnel and a thermometer. The flask was purged with argon, and a solution of isopropylmagnesium chloride (106.12 mmol) in tetrahydrofuran was added dropwise. The solution was stirred under room temperature for 25 minutes and ice-cooled. 1-Bromo-2-chloro-4-(4-chlorophenoxy)benzene (25.000 g, GC purity 98.7%, o-isomer 0.46%) was added dropwise as a tetrahydrofuran (78.6 mL, 1 L/mol) solution, and the mixture was stirred as is for 60 minutes. Methyl 3-bromopyruvate (17.796 g, GC purity 97.7%) was then added dropwise over 25 minutes, and the mixture was stirred under ice cooling for 15 minutes. A 10% aqueous ammonium chloride solution (75 mL), toluene (75 mL), and a 1 N-hydrochloric acid (75 mL) were added to separate the organic layer. The aqueous layer was then extracted with toluene (75 mL×2), the organic layer was washed with water (75 mL), the solvents were distilled off, and a concentrated residue (34.569 g) was obtained.

The concentrated residue (34.569 g) obtained in the above operation and a sodium triazole salt (10.737 g) were placed in a 1000-mL three-neck flask equipped with a thermometer. DMF (78.6 mL, 1 L/mol) was added, the temperature was increased to 60° C., and the mixture was stirred for 3 hours. The reaction solution was cooled, toluene (157 mL, 2 L/mol) and a 10% aqueous ammonium chloride solution (157 mL, 2 L/mol) were added, the mixture was separated, and the aqueous layer was extracted twice with toluene (157 mL, 2 L/mol). Water (157 mL) was added to the organic layer, and the mixture was washed and separated under heating. A concentrate obtained by distilling off the solvents from the organic layer was quantitatively analyzed and found to contain methyl 2-(2-chloro-4-(4-chlorophenoxy)phenyl)-2-hydroxy-3-(1H-1,2,4-triazol-1-yl)propanoate (22.293 g, 69.5% yield).

Synthesis Example 3: Synthesis 1 of 1-bromo-2-chloro-4-(4-chlorophenoxy)benzene

Synthesis of 1-bromo-2-chloro-4-(4-chlorophenoxy)benzene

[Chem. 10]

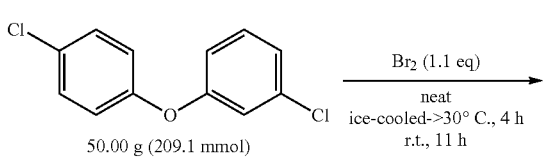

-continued

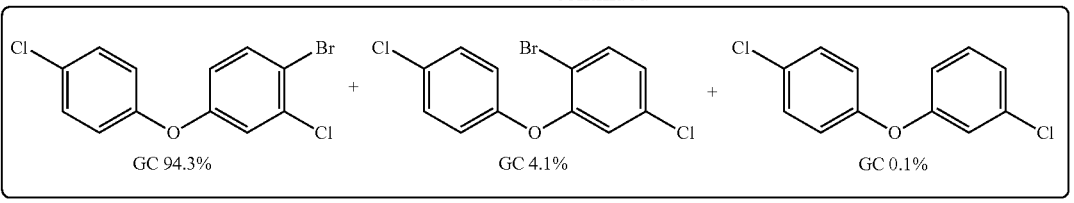

1-Chloro-3-(4-chlorophenoxy)benzene (50.000 g) was placed in a 100-mL three-neck flask equipped with an exhaust gas trap using an Erlenmeyer flask containing an aqueous solution (300 mL) of sodium sulfite (27.8 g) and sodium hydrogen carbonate (18.5 g), a thermometer, and a dropping funnel, and dropwise addition of bromine (36.80 g) was started while the flask was cooled in an ice-water bath. The ice-water bath was removed when the half amount of bromine was added dropwise, and the remaining half was added dropwise under room temperature. After completion of the dropwise addition of bromine, the mixture was heated to 30° C. and stirred for 4 hours. A residual raw material was confirmed by gas chromatography (GC), thus the mixture was allowed to stand at room temperature for another 11 hours, and the raw material was determined to be reduced to 0.07%. The temperature of an oil bath was increased to 65° C. under a stream of nitrogen, the mixture was stirred in the oil bath for 2 hours, and the bromine color almost disappeared. The pressure in the flask was reduced with a diaphragm pump, and the mixture was stirred for 30 minutes and then cooled to room temperature. A seed crystal was added to an oily residue, and a white solid (66.568 g, theoretical yield ratio 100.1%) was obtained. A result of GC analysis showed that the white solid contained 1-bromo-2-chloro-4-(4-chlorophenoxy)benzene (94.3%), 1-bromo-4-chloro-2-(4-chlorophenoxy)benzene (4.1%), and 1-chloro-3-(4-chlorophenoxy)benzene (0.1%).

Purification of 1-bromo-2-chloro-4-(4-chlorophenoxy)benzene

The white solid obtained in the above synthesis was cooled in a refrigerator and pulverized in an agate mortar. The pulverized product was repulp-washed with cooled 2-propanol using a Kiriyama funnel three times (30 mL, 20 mL, and 20 mL), the resulting white solid was dried under reduced pressure, and 1-bromo-2-chloro-4-(4-chlorophenoxy)benzene (56.651 g, 85.2% yield, GC purity 98.7%) was obtained. The residue obtained by drying under reduced pressure contained 1-bromo-4-chloro-2-(4-chlorophenoxy)benzene (0.46%).

$^1$H NMR (400 MHz, CDDl$_3$) δ 7.54 (d, J=8.8 Hz, 1H), 7.35-7.31 (m, 2H), 7.08 (d, J=2.8 Hz, 1 H), 6.98-6.93 (m, 2H), 6.78 (dd, J=8.8 Hz, 2.8 Hz, 1H).

Synthesis Example 4: Synthesis 2 of 1-bromo-2-chloro-4-(4-chlorophenoxy)benzene

[Chem. 11]

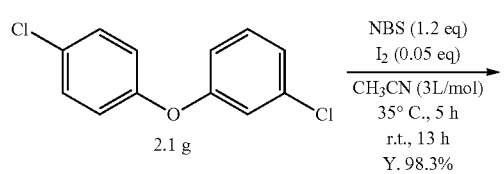

-continued

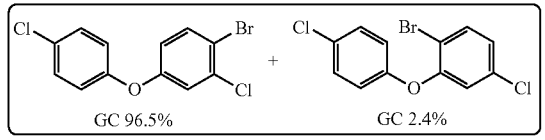

To a solution of 1-chloro-3-(4-chlorophenoxy)benzene (2.100 g) in acetonitrile (26.3 mL, 3 L/mol) was added N-bromosuccinimide (NBS) (1.880 g) and iodine (0.119 g), the mixture was stirred in an oil bath at 35° C. for 5 hours and then allowed to stand under room temperature for 13 hours. To the reaction solution was added a 10% aqueous sodium thiosulfate solution (4 mL), and the iodine color disappeared. Water (30 mL) was added, the solution was extracted with hexane (20 mL×2), and the extract was washed sequentially with water (20 mL) and a saturated brine solution (20 mL). The extract was dried with Na$_2$SO$_4$, the solvents were distilled off, and a white solid (2.744 g, theoretical yield ratio 98.3%). A result of GC analysis showed that the white solid contained 1-bromo-2-chloro-4-(4-chlorophenoxy)benzene (96.5%) and 1-bromo-4-chloro-2-(4-chlorophenoxy)benzene (2.4%).

Synthesis Example 5: Synthesis 3 of 1-bromo-2-chloro-4-(4-chlorophenoxy)benzene

[Chem. 12]

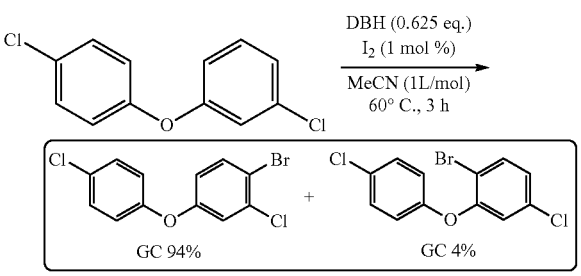

Under a nitrogen atmosphere, 2.1 mL of acetonitrile was added to 1-chloro-3-(4-chlorophenoxy)benzene (0.499 g). While the mixture was stirred under room temperature, 1,3-dibromo-5,5-dimethylhydantoin (DBH) (0.374 g) and iodine (0.005 g) were added, temperature was increased to 60° C., and then the mixture was stirred for 3 hours. The reaction was then stopped by adding a 10% aqueous sodium thiosulfate solution and water. The mixture was extracted with toluene, and the organic layer was washed with a saturated brine solution and dried with anhydrous sodium sulfate. The solvents were distilled off, and a crude product (0.659 g, 99.1% crude yield) was obtained. A result of GC analysis showed that the crude product contained 1-bromo chloro-4-(4-chlorophenoxy)benzene (94%) and 1-bromo-4-chloro-2-(4-chlorophenoxy)benzene (4%).

Synthesis Example 6: Regeneration of
1-chloro-3-(4-chlorophenoxy)benzene from Repulp Wash Solution

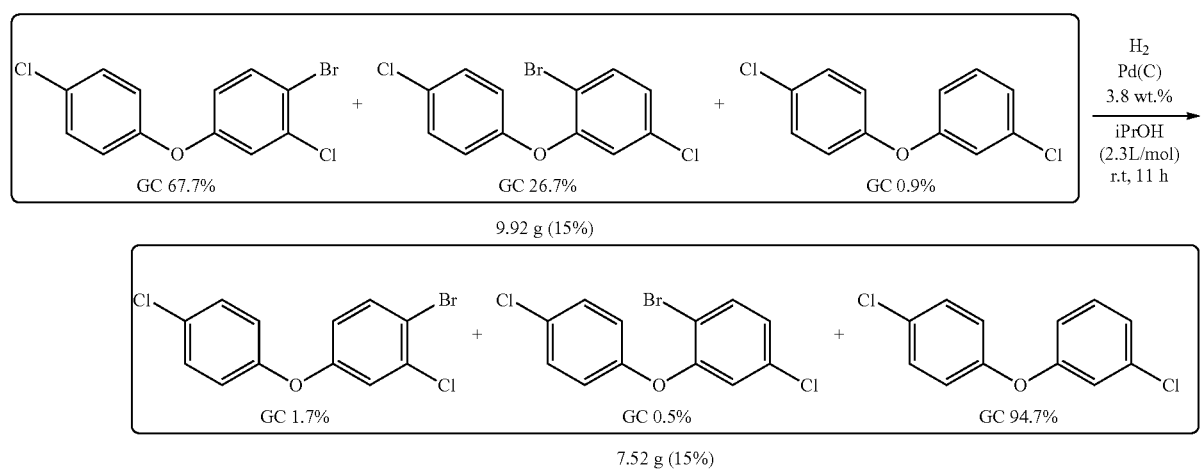

A repulp wash solution, the filtrate resulting from the repulp washing in Synthesis Example 3 described above, was concentrated, and an oily substance (9.917 g) was obtained. A result of GC analysis showed that the oily substance contained 1-bromo-2-chloro-4-(4-chlorophenoxy)benzene (67.7%), 1-bromo-4-chloro-2-(4-chlorophenoxy)benzene (26.7%), and 1-chloro-3-(4-chlorophenoxy)benzene (0.9%). The oily substance (9.917 g) and the same amount of 2-propanol (70 mL, 2.25 L/mol) used in the repulp washing were placed in a 200-mL three-neck flask equipped with a thermometer, a 5% palladium on carbon catalyst (0.372 g, available from Kawaken Fine Chemicals Co., Ltd., EA, water content 54.9%) was added, and the mixture was stirred under a hydrogen atmosphere for 11 hours. As a result, the residual amount of 1-bromo-4-chloro-2-(4-chlorophenoxy)benzene was reduced to 1% or lower. The catalyst was removed by filtration with a Hyflo Super-Cel, the solvent was distilled off, and then the substance was dissolved in toluene (20 mL). The solution was washed with water (20 mL), and 1-chloro-3-(4-chlorophenoxy)benzene (7.516 g, theoretical yield ratio 101.6%, GC purity 94.7%, 1.7% of 1-bromo-2-chloro-4-(4-chlorophenoxy)benzene, 0.5% of 1-bromo-4-chloro-2-(4-chlorophenoxy)benzene) was obtained.

Synthesis Example 7: Bromination of
1-chloro-3-(4-chlorophenoxy)benzene Regenerated from Repulp Wash Solution and Purification of Brominated Product

[Chem. 14]
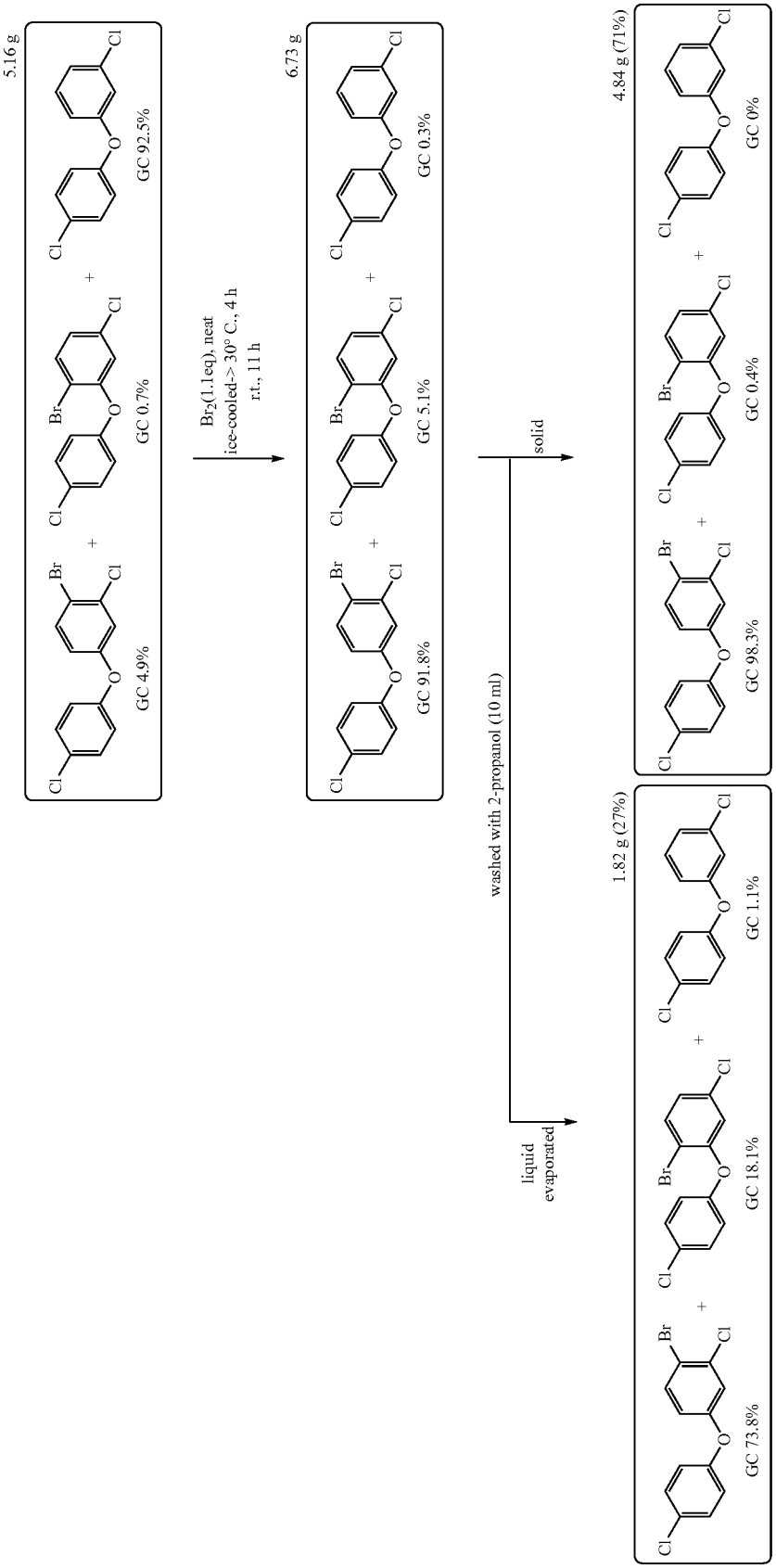

A hydrogenated compound (5.163 g, 4.9% of 1-bromo-2-chloro-4-(4-chlorophenoxy)benzene, 0.7% of 1-bromo-4-chloro-2-(4-chlorophenoxy)benzene, and 92.5% of 1-chloro-3-(4-chlorophenoxy)benzene) of the concentrated oily substance of the repulp wash solution was placed in a 25-mL three-neck flask equipped with an exhaust gas trap using an Erlenmeyer flask containing an aqueous solution of sodium sulfite (3.0 g) and sodium hydrogen carbonate (2.0 g) and a dropping funnel, bromine (3.80 g) was added dropwise while the flask was cooled in an ice-water bath, and then the mixture was heated to 30° C. and stirred for 4 hours. The mixture was allowed to stand at room temperature for 11 hours, the raw material was confirmed to be reduced to 0.34%. The temperature of an oil bath was increased to 65° C. under a stream of nitrogen, the mixture was stirred in the oil bath for 1.5 hours, and the bromine color almost disappeared. The pressure in the flask was reduced with a diaphragm pump, and the mixture was stirred for 30 minutes and then cooled to room temperature. The white solid (6.729 g, theoretical yield ratio 98.0%) obtained by adding a seed crystal to the oily residue was obtained. A result of GC analysis showed that the white solid contained 1-bromo-2-chloro-4-(4-chlorophenoxy)benzene (91.8%), 1-bromo-4-chloro-2-(4-chlorophenoxy)benzene (5.1%), and 1-chloro-3-(4-chlorophenoxy)benzene (0.3%). The resulting white solid was cooled in a refrigerator, pulverized in an agate mortar, and repulp-washed with cooled 2-propanol (10 mL) using a Kiriyama funnel. The resulting white solid was dried under reduced pressure, and 1-bromo-2-chloro-4-(4-chlorophenoxy)benzene (4.841 g, 70.5% yield, GC purity 98.3%, 0.4% of 1-bromo-4-chloro-2-(4-chlorophenoxy)benzene) was obtained. The repulp wash solution was concentrated, and an oily substance (1.820 g, GC purity 73.8%, 18.1% of 1-bromo-4-chloro-2-(4-chlorophenoxy)benzene, 1.1% of 1-chloro-3-(4-chlorophenoxy)benzene) was obtained.

Synthesis Example 8: Synthesis of methyl 2-(2-chloro-4-(4-chlorophenoxy)phenyl)-2-hydroxy-3-(1H-1,2,4-triazol-1-yl)propanoate Synthesis of 1-bromo-2-chloro-4-(4-chlorophenoxy)benzene

[Chem. 15]

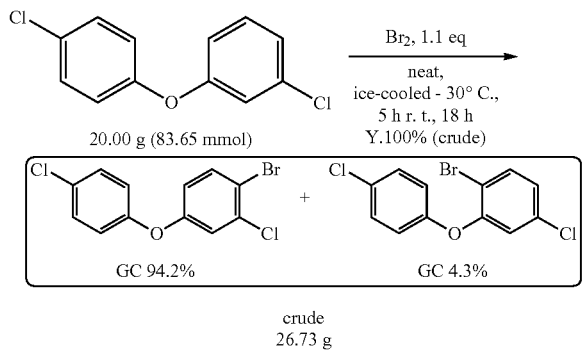

1-Chloro-3-(4-chlorophenoxy)benzene (20.00 g) was placed in a 50-mL three-neck flask equipped with an exhaust gas trap using an Erlenmeyer flask containing an aqueous solution (100 mL) of sodium sulfite (11.3 g) and sodium hydrogen carbonate (7.38 g), a thermometer, and a dropping funnel, and dropwise addition of bromine (14.71 g) was started while the flask was cooled in an ice-water bath. The ice-water bath was removed when the half amount of bromine was added dropwise, and the remaining half was added dropwise under room temperature. After completion of the dropwise addition of bromine, the mixture was heated to 30° C. and stirred for 5 hours. The mixture was allowed to stand at room temperature for 18 hours, the raw material was confirmed by GC to be reduced to 0.60%. The temperature of an oil bath was increased to 60° C. under a stream of nitrogen, the mixture was stirred in the oil bath for 2 hours, and the bromine color almost disappeared. The pressure in the flask was reduced with a diaphragm pump at the same temperature, the mixture was stirred for 30 minutes and then cooled to room temperature, the mixture was distilled under reduced pressure, and an oily substance (26.735 g) was thus obtained. The oily substance contained 1-bromo-2-chloro-4-(4-chlorophenoxy)benzene (94.2%), 1-bromo-4-chloro-2-(4-chlorophenoxy)benzene (4.3%), and 1-chloro-3-(4-chlorophenoxy)benzene (0.4%).

Synthesis of methyl 2-(2-chloro-4-(4-chlorophenoxy)phenyl)-2-hydroxy-3-(1H-1,2,4-triazol-1-yl)propanoate

[Chem. 16]

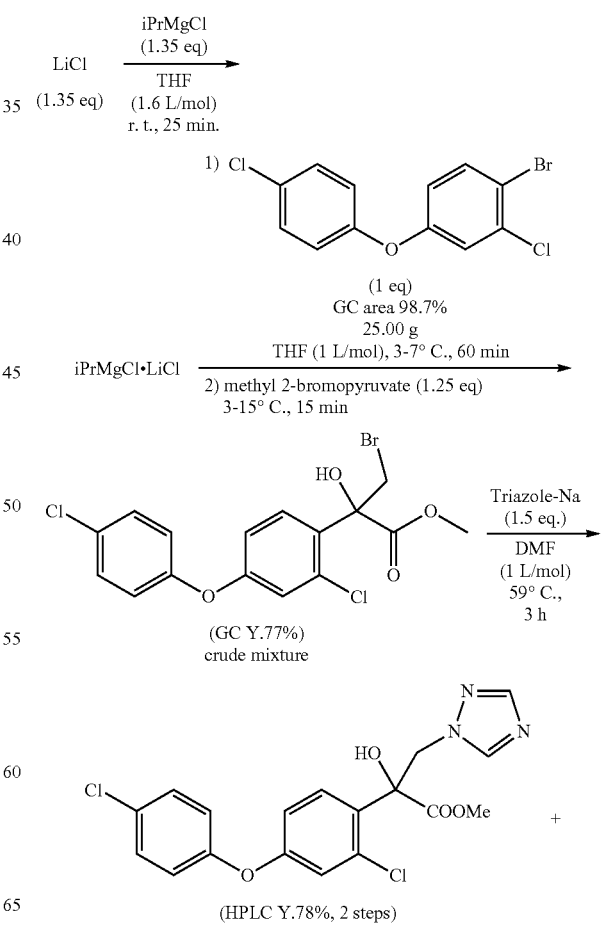

-continued

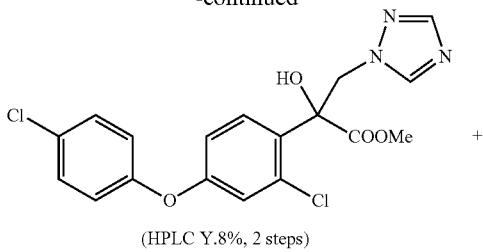

(HPLC Y.8%, 2 steps)

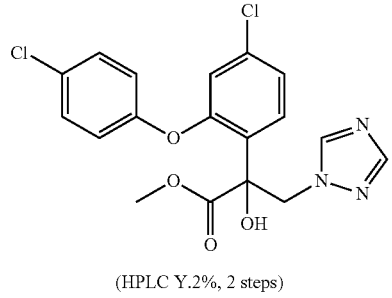

(HPLC Y.2%, 2 steps)

Lithium chloride (0.720 g, vacuum-dried at 130° C. for 6 hours) was weighed under a stream of nitrogen and sealed in a 50-mL three-neck flask equipped with a dropping funnel and a thermometer. The flask was purged with argon, and a solution of isopropylmagnesium chloride (0.965 mol/L, 17.60 mL, 16.99 mmol) in tetrahydrofuran was added dropwise. The solution was stirred under room temperature for 25 minutes and ice-cooled. 1-Bromo-2-chloro-4-(4-chlorophenoxy)benzene (4.001 g, GC purity: 94.2%, 1-bromo-4-chloro-2-(4-chlorophenoxy)benzene: 4.3%, 1-chloro-3-(4-chlorophenoxy)benzene: 0.4%) was added dropwise as a tetrahydrofuran (12.6 mL, 1 L/mol) solution, and the mixture was stirred as is for 60 minutes. Methyl 3-bromopyruvate (2.856 g, GC purity 97.1%) was added dropwise over 15 minutes, and the mixture was stirred under ice cooling for 15 minutes. A 10% aqueous ammonium chloride solution (12 mL), toluene (12 mL), and a 1 N-hydrochloric acid (12 mL) were added to separate the organic layer. The aqueous layer was then extracted with toluene (12 mL×2), the organic layer was washed with water (12 mL), the solvents were distilled off, and a concentrated residue (5.640 g) was obtained.

The concentrated residue (5.640 g) obtained in the above operation and a sodium triazole salt (1.718 g) were placed in a 50-mL three-neck flask equipped with a thermometer. DMF (12.6 mL, 1 L/mol) was added, the temperature was increased to 60° C., and the mixture was stirred for 3 hours. The reaction solution was cooled, toluene (25 mL, 2 L/mol) and a 10% aqueous ammonium chloride solution (25 mL, 2 L/mol) were added, the solution was separated, and the aqueous layer was extracted twice with toluene (25 mL, 2 L/mol). Water (25 mL) was added to the organic layer, and the mixture was washed and separated twice under heating. A concentrate (4.562 g) obtained by distilling off the solvents from the organic layer was quantitatively analyzed and found to contain the target methyl 2-(2-chloro-4-(4-chlorophenoxy)phenyl)-2-hydroxy-3-(1H-1,2,4-triazol-1-yl)propanoate (3.319 g).

INDUSTRIAL APPLICABILITY

The present invention can be used in synthesis of an azole derivative useful as an agricultural chemical.

The invention claimed is:
1. A method of producing 1-chloro-3-(4-chlorophenoxy)benzene, wherein 1-chloro-3-(4-chlorophenoxy)benzene is obtained by performing hydrogenation reduction of 1-bromo-2-chloro-4-(4-chlorophenoxy)benzene or 1-bromo-4-chloro-2-(4-chlorophenoxy)benzene.

* * * * *